US009803167B2

(12) United States Patent
Choi et al.

(10) Patent No.: US 9,803,167 B2
(45) Date of Patent: Oct. 31, 2017

(54) STRETCHING APPARATUS AND METHOD FOR ALIGNING MICROFIBRILS

(71) Applicant: KOREA INSTITUTE OF SCIENCE AND TECHNOLOGY, Seoul (KR)

(72) Inventors: Nakwon Choi, Seoul (KR); Eun-Mi Hur, Seoul (KR); Sohyun Kim, Seoul (KR); Sun-Kyoung Im, Seoul (KR); Eui Sung Yoon, Seoul (KR); Changjoon Justin Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 127 days.

(21) Appl. No.: 14/950,710

(22) Filed: Nov. 24, 2015

(65) Prior Publication Data
US 2016/0152946 A1   Jun. 2, 2016

(30) Foreign Application Priority Data

Nov. 28, 2014   (KR) .................. 10-2014-0168311

(51) Int. Cl.
| | |
|---|---|
| *B29C 55/00* | (2006.01) |
| *C12M 1/42* | (2006.01) |
| *B29C 55/02* | (2006.01) |
| *B29C 55/20* | (2006.01) |
| *B29C 55/12* | (2006.01) |
| *C08J 5/00* | (2006.01) |

(Continued)

(52) U.S. Cl.
CPC ........... *C12M 35/04* (2013.01); *A61L 27/165* (2013.01); *A61L 27/383* (2013.01);
(Continued)

(58) Field of Classification Search
CPC ...... C12M 35/04; B29C 55/02; B29C 55/023; B29C 55/12; B29C 55/20
(Continued)

(56) References Cited

U.S. PATENT DOCUMENTS

| | | | |
|---|---|---|---|
| 6,544,762 | B1 | 4/2003 | Tranquillo et al. |
| 8,597,717 | B2 | 12/2013 | Fuller et al. |

(Continued)

FOREIGN PATENT DOCUMENTS

| | | |
|---|---|---|
| JP | 5-7487 A | 1/1993 |
| JP | 2003-61642 A | 3/2003 |

(Continued)

OTHER PUBLICATIONS

Lee, Philip, et al. "Microfluidic Alignment of Collagen Fibers in vitro Cell Culture." Biomedical Microdevices 8.1 (2006): 35-41. (7 pages in English).

(Continued)

*Primary Examiner* — Timothy Kennedy
(74) *Attorney, Agent, or Firm* — NSIP Law

(57) ABSTRACT

The present disclosure relates to stretching apparatus and method for aligning microfibrils. Specifically, the present disclosure provides an apparatus for aligning microfibrils along a single direction, which includes: a first elastic substrate onto which a composition containing microfibrils is loaded; and a stretching module which stretches the width of the elastic substrate. In accordance with the apparatus the present disclosure, microfibrils or cells may be aligned along a particular direction simply by pulling and then releasing the elastic substrate. The present disclosure is also useful for culturing of the aligned cells because the physiological activity of the cells can be maintained and cytotoxicity can be prevented.

15 Claims, 25 Drawing Sheets

(51) Int. Cl.
   *A61L 27/16* (2006.01)
   *A61L 27/38* (2006.01)
   *A61L 27/50* (2006.01)
(52) U.S. Cl.
   CPC ....... *A61L 27/3804* (2013.01); *A61L 27/3826* (2013.01); *A61L 27/3834* (2013.01); *A61L 27/50* (2013.01); *B29C 55/02* (2013.01); *B29C 55/023* (2013.01); *B29C 55/12* (2013.01); *B29C 55/20* (2013.01); *C08J 5/00* (2013.01); *A61L 2430/32* (2013.01)
(58) Field of Classification Search
   USPC .................................. 264/40.1, 291
   See application file for complete search history.

(56) References Cited

U.S. PATENT DOCUMENTS

| | | | |
|---|---|---|---|
| 8,691,262 | B2 | 4/2014 | Harris |
| 2003/0219800 | A1* | 11/2003 | Beske ............... G01N 33/5008 506/10 |
| 2004/0235153 | A1 | 11/2004 | Takagi et al. |
| 2010/0311949 | A1 | 12/2010 | Akkus et al. |
| 2011/0306754 | A1 | 12/2011 | Cheng et al. |
| 2014/0147494 | A1 | 5/2014 | Cheng |
| 2016/0032234 | A1* | 2/2016 | Rosell Ferrer ......... C12M 35/04 435/173.8 |

FOREIGN PATENT DOCUMENTS

| | | |
|---|---|---|
| JP | 2009-517112 A | 4/2009 |
| KR | 10-2007-0116105 A | 12/2007 |
| WO | WO 2006/097751 A2 | 9/2006 |
| WO | WO 2007/060459 A2 | 5/2007 |
| WO | WO 2009/073548 A1 | 6/2009 |

OTHER PUBLICATIONS

Guo, Cheng, et al. "Flow and Magnetic Field Induced Collagen Alignment." ScienceDirect, Biomaterials 28.6 (2007): 1105-1114. (10 pages in English).

* cited by examiner

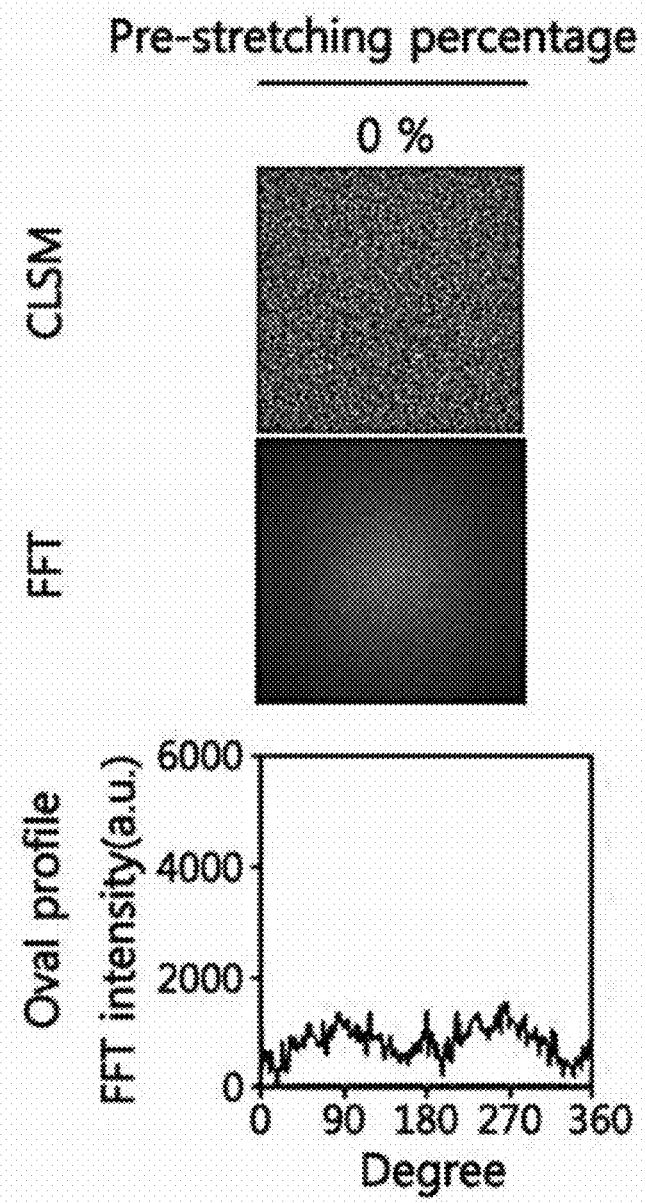

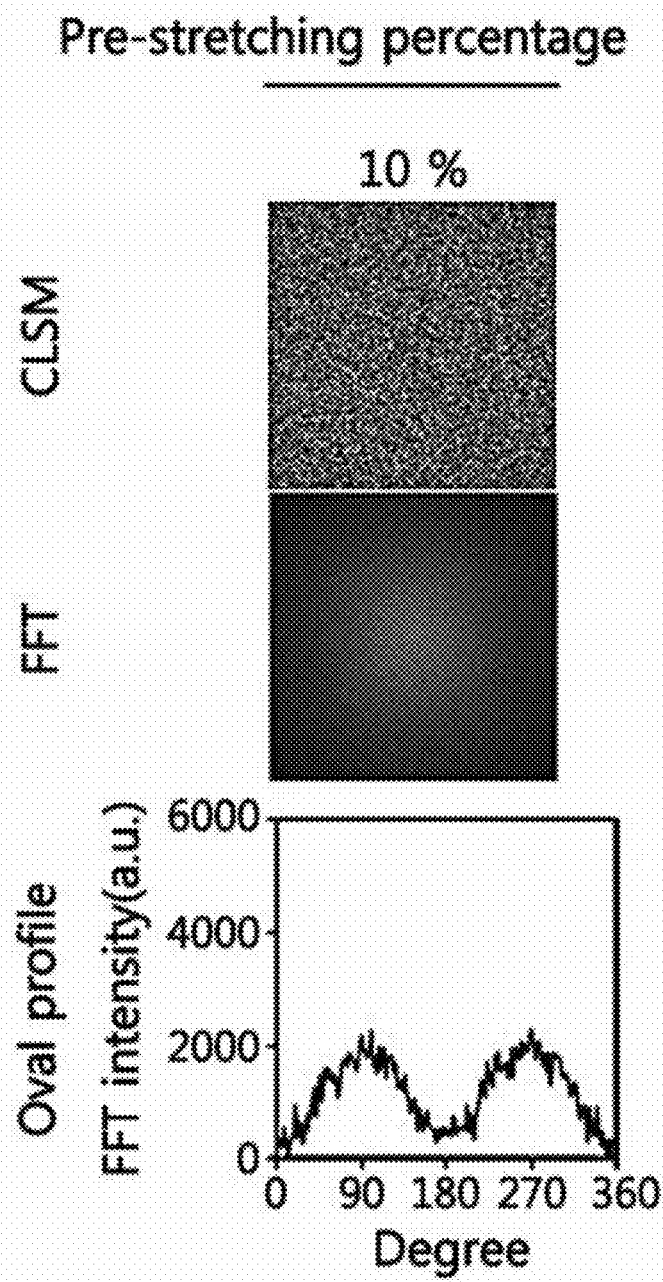

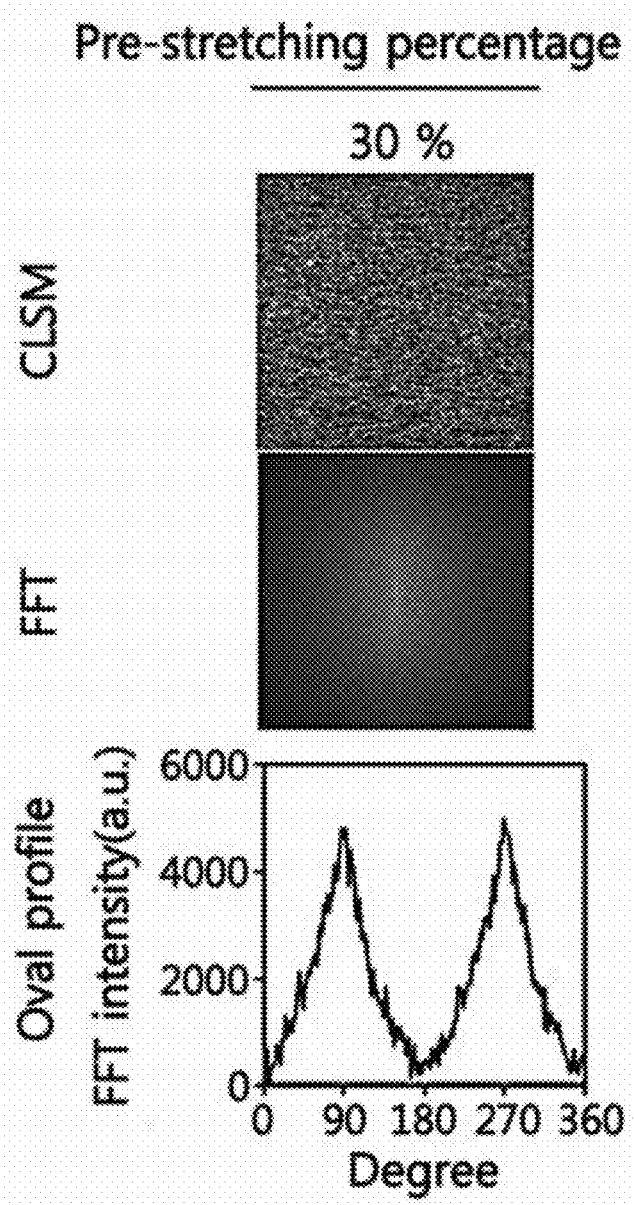

STRETCHING APPARATUS AND METHOD FOR ALIGNING MICROFIBRILS

CROSS-REFERENCE TO RELATED APPLICATION

This application claims the priority of Korean Patent Application No. 10-2014-0168311, filed on Nov. 28, 2014, and all the benefits accruing therefrom under 35 U.S.C. §119, the contents of which in its entirety are herein incorporated by reference.

BACKGROUND

1. Field

The present disclosure relates to stretching apparatus and method for aligning microfibrils.

2. Description about National Research and Development Support

This study was supported by the Brain Science Source Technology Project of the Ministry of Science, ICT and Future Planning, Republic of Korea (Development of Non-invasive/Cell selective stimulate measuring technology and Establishment of brain disease model by using Optogenetics method, Project No. 1711003291) under the superintendence of Korea Institute of Science and Technology.

3. Description of the Related Art

All human organs and tissues are generated from the embryo through developmental stages during which cells and extracellular matrices surrounding the cells are aligned characteristically. Due to these structural characteristics, the cells existing in each organ and tissue interact characteristically with nearby other cells or extracellular matrices surrounding the cells. This interaction is critical in the functioning of each organ. As representative examples, the brain, heart, central and peripheral nerve fascicles and muscles show very characteristic structures. Collapse of these structures leads to severe developmental disorder. Since the technical concept of tissue engineering of embedding and culturing cells in a hydrogel, inducing them to grow similarly to a specific tissue and then transplanting the tissue into an organism was first reported in 1993 in the journal Science, three-dimensional culturing of animal cells is being developed continuously mainly in the US as a method of culturing cells in various synthetic or natural polymeric biomaterials. For such organs as the liver, cartilage, kidneys, etc., attempts to establish physiological models under an environment more similar to the in vivo environment than the existing two-dimensional culturing method have been successful to some extent. The three-dimensional culturing technology has been introduced not only for the normal organ models but also to establish pathological models, for example, mimicking the cellular microenvironment in a cancerous tissue, and the intercellular interaction and interaction between cells and the extracellular matrices that have been overlooked in the existing two-dimensional culturing are being studied consistently. Since the mid-2000s, its application has extended to three-dimensional culturing of stem cells. Especially, the brain is a complicated, but highly characteristically structured organ. The cell bodies of specific neurons are selectively distributed in a specific layer in the brain and the axons and dendrites extruding from the neuron are aligned regularly along a specific direction. This structural characteristic plays a critical role in the signal transmission of the brain nerve tissue/network. It is known that abnormal alignment and structuring of the cranial nerve network during the embryonic period lead to various mental disorders including autism. Representative technologies currently used to study the alignment of neural networks are in utero electroporation and organotypic slice culture. However, these methods are very invasive and labor-intensive and it is impossible to monitor the long period of developmental stages. In addition, because they are optimized to study specific regions in the brain, it is difficult to study other regions in the brain. With the brain mapping project recently started in the US and Europe, efforts to embody the brain nerve tissue/network in a three-dimensional ex vivo environment are actively made. Accordingly, development of a technology that allows for the culturing of neurons and glial cells that constitute the brain in an aligned biomaterial structure is important and its demand will increase consistently. A representative biomaterial used for cell culturing is collagen, which is a fibrous material making up the largest part of the human extracellular matrix. Currently known technologies for aligning collagen fiber include application of 1) electric field or 2) magnetic field from an external apparatus, 3) contraction of collagen using cells embedded in the collagen and 4) flowing a collagen solution through a narrow tube to utilize the force generated by fluid flow (shear force). However, the application of electric or magnetic field from an external apparatus may lack reproducibility and practicability and the cells stimulated by the electric or magnetic field may exhibit altered physiological activity and significant toxicity. In addition, with the methods described above, it is difficult to manufacture different types of collagen into an integrated three-dimensional structure with desired shape and size and to align the collagen fibers at the same time.

REFERENCES OF THE RELATED ART

Patent Documents

WO2009073548 A1.
U.S. Pat. No. 6,544,762 B1.
U.S. Pat. No. 8,691,262 B2.
U.S. Pat. No. 8,597,717 B2.

SUMMARY

The present disclosure is directed to providing an apparatus and a method for aligning microfibrils and maintaining survivability of cells aligned by the microfibrils.

In an aspect, the present disclosure provides an apparatus for aligning microfibrils, as an apparatus for aligning microfibrils on a substrate along a single direction, which includes a first elastic substrate onto which a composition containing microfibrils is loaded.

In another aspect, the present disclosure provides a method for aligning microfibrils along a single direction, which includes: (1) a step of stretching an elastic substrate; (2) a step of loading a composition containing microfibrils onto the stretched elastic substrate; and (3) a step of restoring the elastic substrate.

In accordance with the apparatus or method of the present disclosure, microfibrils or cells may be aligned along a particular direction simply by pulling and then releasing the elastic substrate. The present disclosure is also useful for culturing of the aligned cells because the physiological activity of the cells can be maintained and cytotoxicity can be prevented. In addition, the apparatus or method of the present disclosure is advantageous in that more than one cell and collagen which are contained not only in a single collagen solution but also in multiple collagen solutions can be aligned at the same time. Accordingly, cell culture models used in various researches can be easily produced and provided on a large. In addition, the present disclosure is very useful because it can be used to align and culture neurons and glial cells of the brain which are very sensitive to environmental change.

BRIEF DESCRIPTION OF THE DRAWINGS

FIG. 3A is a perspective view of an apparatus for aligning microfibrils according to an aspect of the present disclosure.

FIG. 3B shows that the length of an assembly or disassembly is increased (by ΔL) when a handle 5 in FIG. 3A is pulled from opposite directions. A fixture 6 is disposed between a bar or support 4 to maintain the increased length.

FIG. 3C shows an unaligned composition containing microfibrils (shown in red color) loaded onto a stretched elastic substrate.

FIG. 3D shows that the composition containing microfibrils is aligned along a single direction when the fixture 6 is removed as the substrate is restored to its original state.

FIG. 5A shows a microscopic image and an oval profile of collagen when pre-stretching was not conducted.

FIG. 5B shows a microscopic image and an oval profile of collagen when an elastic substrate was pre-stretched by 10% of its original width using an apparatus for aligning microfibrils of the present disclosure.

FIG. 5D shows a microscopic image and an oval profile of collagen when an elastic substrate was pre-stretched by 30% of its original width using an apparatus for aligning microfibrils of the present disclosure.

DETAILED DESCRIPTION OF MAIN ELEMENTS

Figure 1A:
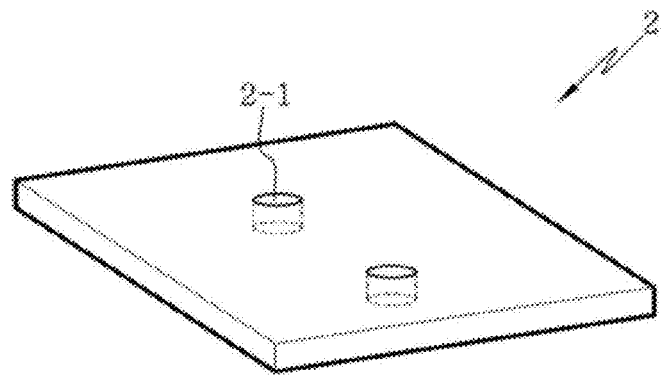
FIG. 1A shows a second elastic substrate of an apparatus for aligning microfibrils according to an aspect of the present disclosure.

1: first elastic substrate
1-1: well of first elastic substrate in which composition containing microfibrils is loaded
2: second elastic substrate
2-1: hole of second elastic substrate
3: assembly or disassembly of first elastic substrate and second elastic substrate
4: bar or support for adjusting height of first elastic substrate or assembly or disassembly of first elastic substrate and second elastic substrate and handle 5: handle
6: fixture
7: composition containing microfibrils
8: stretcher
9: controller
10: stretching module

DETAILED DESCRIPTION

In an aspect, the present disclosure may relate to an apparatus for aligning microfibrils along a single direction, which includes: a first elastic substrate onto which a composition containing microfibrils is loaded; and a stretching module which stretches the width of the elastic substrate.

In an aspect of the present disclosure, the first elastic substrate may include a well in which the composition containing microfibrils is loaded.

In an aspect of the present disclosure, the elastic substrate comprises an elastomer or may be formed of an elastomer.

In an aspect of the present disclosure, the elastic substrate may mean the first elastic substrate, a second elastic substrate or an assembly (or disassembly) of the first elastic substrate and the second elastic substrate.

In an aspect of the present disclosure, the elastomer may be one or more selected from a group consisting of natural polyisoprene, synthetic polyisoprene, polybutadiene, chloroprene rubber, butyl rubber, styrene-butadiene rubber, nitrile rubber, ethylene propylene rubber, ethylene propylene diene rubber, epichlorohydrin rubber, polyacrylic rubber, silicone rubber, fluorosilicone rubber, fluoroelastomers, polyether block amides, chlorosulfonated polyethylene, ethylene-vinyl acetate and polydimethylsiloxane. Specifically, in an aspect of the present disclosure, the elastomer constituting the elastic substrate may be any elastic material which is widely known in the art or which can be easily selected by those skilled in the art. Examples include natural polyisoprene, synthetic polyisoprene, polybutadiene, chloroprene rubber (polychloroprene or neoprene), butyl rubber (a copolymer of isobutylene and isoprene), halogenated butyl rubber (chlorobutyl rubber or bromobutyl rubber), styrene-butadiene rubber, nitrile rubber (a copolymer of butadiene and acrylonitrile), hydrogenated nitrile rubber, ethylene propylene rubber (a copolymer of ethylene and propylene), ethylene propylene diene rubber (a terpolymer of ethylene, propylene and a diene component), epichlorohydrin rubber, polyacrylic rubber, silicone rubber, fluorosilicone rubber, fluoroelastomers (Viton, Technoflon, etc.), perfluoroelastomers, polyether block amides, chlorosulfonated polyethylene, ethylene-vinyl acetate, etc.

In an aspect of the present disclosure, the microfibril may be one or more synthetic polymer fiber selected from a group consisting of nylon, polyacrylic acid, polycarbonate, polyurethane, poly(ethylene-vinyl acetate), polystyrene, polyvinyl alcohol, cellulose acetate and polyethylene oxide or one or more natural polymer fiber selected from a group consisting of elastin, gelatin, fibrinogen, fibrin, alginate, cellulose, silk fibroin, chitosan, laminin, actin and collagen. Specifically, in an aspect of the present disclosure, the microfibril is not particularly as long as it is a fiber having directionality that can be used in culturing of cells. In particular, the microfibrils may be a collagen fiber.

In an aspect of the present disclosure, the composition containing microfibrils may further contain one or more types of cells.

In an aspect of the present disclosure, the cell may be a cell that can be cultured ex vivo (or in vitro) and can be obtained from a living organism. Specifically, the cell may be one or more selected from a group consisting of a neuron, a glial cell, a muscle cell, a solid cancer cell, a mesenchymal stem cell and a fibroblast. In an aspect of the present disclosure, the cell may be a neuron, a glial cell, a muscle cell, a solid cancer cell, a mesenchymal stem cell or a fibroblast.

In the present disclosure, the cell is not particularly limited as long as it is a cell that can be cultured ex vivo and can be obtained from a living organism. Any cell that can be used for alignment or arrangement of cells in the art can be used without limitation.

In an aspect of the present disclosure, the apparatus may further include a second elastic substrate which is assembled on or disassembled on the first elastic substrate.

In an aspect of the present disclosure, the second elastic substrate may have the same elasticity and size as the first elastic substrate.

In an aspect of the present disclosure, the second elastic substrate may have two or more holes, wherein the hole is a hole for loading the composition containing microfibrils onto the first elastic substrate.

In an aspect of the present disclosure, the stretching module may include: a handle which grips both ends of the elastic substrate; a stretcher which stretches the elastic substrate by operating the handle; and a controller which controls the movement of the stretcher.

In an aspect of the present disclosure, the controller may stretch the elastic substrate by 5-80% of its width by operating the stretcher. Specifically, the controller may stretch the elastic substrate by 5% or more, 10% or more, 15% or more, 20% or more, 25% or more, 27% or more, 29% or more, 30% or more, 32% or more, 34% or more, 36% or more, 38% or more, 40% or more, 42% or more, 44% or more, 46% or more, 48% or more, 50% or more, 52% or more, 54% or more, 56% or more, 58% or more, 60% or more, 65% or more, 70% or more or 80% or more, or 80% or less, 70% or less, 65% or less, 60% or less, 58% or less, 56% or less, 54% or less, 52% or less, 50% or less, 48% or less, 46% or less, 44% or less, 42% or less, 40% or less, 38% or less, 36% or less, 34% or less, 32% or less, 30% or less, 28% or less, 26% or less, 24% or less, 22% or less, 20% or less, 15% or less, 10% or less or 5% or less of its width, as compared to before the stretching.

In an aspect of the present disclosure, when the first elastic substrate is assembled with the second elastic substrate, the handle grips the ends of the two substrates and the first elastic substrate and the second elastic substrate are stretched together.

In an aspect of the present disclosure, the controller may, after stretching the width of the first elastic substrate by operating the stretcher, maintain the stretched state for 1-10 minutes when the composition comprising microfibrils is loaded onto the first elastic substrate and then restore the first elastic substrate. Specifically, the controller may maintain the stretched state of the elastic substrate for 1 minute or longer, 2 minutes or longer, 3 minutes or longer, 4 minutes or longer, 5 minutes or longer, 6 minutes or longer, 7 minutes or longer, 8 minutes or longer, 9 minutes or longer, 10 minutes or longer, 20 minutes or longer, 30 minutes or longer, 40 minutes or longer or 1 hour or longer, or 1 hour or shorter, 40 minutes or shorter, 30 minutes or shorter, 20 minutes or shorter, 10 minutes or shorter, 9 minutes or shorter, 8 minutes or shorter, 7 minutes or shorter, 6 minutes or shorter, 5 minutes or shorter, 4 minutes or shorter, 3 minutes or shorter, 2 minutes or shorter or 1 minute or shorter.

In an aspect of the present disclosure, the stretching module may further include a support (or a bar) having a height corresponding to the difference between the height of the first elastic substrate and the height of the handle.

In an aspect of the present disclosure, the stretching module may further include a fixture which is disposed between the support and maintains the stretched state of the first elastic substrate.

In an aspect of the present disclosure, the microfibrils may be aligned to be perpendicular to the stretching direction of the elastic substrate.

In an aspect of the present disclosure, the first elastic substrate may further have an adhesive coated on its surface.

In an aspect of the present disclosure, the adhesive may be one or more selected from a group consisting of glutaraldehyde, polyethylenimine, poly-L-lysine, poly-D-lysine and polydopamine. However, any adhesive widely known in the art that can be used to fix a composition containing microfibrils such as a collagen gel in the well of the elastic substrate or one that can be easily selected by those skilled in the art can be used without limitation.

In an aspect of the present disclosure, the stretching module is not limited as long as it is one that can stretch the width of the elastic substrate, which is widely known in the art or can be easily selected by those skilled in the art. For example, a hydraulic cylinder or a pneumatic cylinder may be used. In an aspect of the present disclosure, the handle is not limited as long as it can grip the both ends of the elastic substrate and stretch it.

In an aspect, the present disclosure may relate to a method for aligning microfibrils along a single direction, which includes: (1) a step of stretching an elastic substrate; (2) a step of loading a composition containing microfibrils onto the stretched elastic substrate; and (3) a step of restoring the elastic substrate.

In an aspect of the present disclosure, the method may further include, before the step (1), (1)' a step of coating the elastic substrate with an adhesive.

In an aspect of the present disclosure, the method may further include, after the step (2) and before the step (3), (2)' a step of maintaining the stretched state of the substrate onto which the composition containing microfibrils is loaded.

In an aspect of the present disclosure, in the step (2)', the stretched state of the elastic substrate may be maintained for 1-10 minutes. Specifically, in the step (2)', the stretched state of the elastic substrate may be maintained for 1 minute or longer, 2 minutes or longer, 3 minutes or longer, 4 minutes or longer, 5 minutes or longer, 6 minutes or longer, 7 minutes or longer, 8 minutes or longer, 9 minutes or longer, 10 minutes or longer, 20 minutes or longer, 30 minutes or longer, 40 minutes or longer or 1 hour longer, or 1 hour or shorter, 40 minutes or shorter, 30 minutes or shorter, 20 minutes or shorter, 10 minutes or shorter, 9 minutes or shorter, 8 minutes or shorter, 7 minutes or shorter, 6 minutes or shorter, 5 minutes or shorter, 4 minutes or shorter, 3 minutes or shorter, 2 minutes or shorter or 1 minute or shorter.

In an aspect of the present disclosure, in the step (2)', the composition containing microfibrils may be cured partially as the stretched state of the elastic substrate is maintained.

In an aspect of the present disclosure, in the step (3), the microfibrils may be aligned along a direction parallel to the stretching or restoring direction.

In an aspect of the present disclosure, the method may further include, after the step (3), (3)' a step of gelling the composition containing microfibrils. The step (3)' may be performed between the step (3) and a step (4) described below. Specifically, in an aspect of the present disclosure, the step (3)' may be performed by keeping the restored elastic substrate in an incubator at 30-40° C., specifically at 37° C., for 10 minutes to 1 hour, for 20-40 minutes or for 30 minutes.

In an aspect of the present disclosure, the method may further include, after the step (3), (4) a step of incubating the elastic substrate having the microfibrils aligned in a cell culture medium. Specifically, the step (4) may be performed in an incubator. The incubation time may be 1-5 days, specifically 2-4 days or about 3 days and the incubation temperature may be 30-40° C., specifically 35-39° C., more specifically 36-38° C.

In an aspect of the present disclosure, the elastic substrate may include a well in which the composition containing microfibrils is loaded.

In an aspect of the present disclosure, in the step (2), the composition containing microfibrils may be loaded in the well of the elastic substrate.

In an aspect of the present disclosure, in the step (1), the elastic substrate may be stretched by 5-80% of its width as compared to before the stretching. Specifically in an aspect of the present disclosure, in the step (1), the elastic substrate may be stretched by 5% or more, 10% or more, 15% or more, 20% or more, 25% or more, 27% or more, 29% or more, 30% or more, 32% or more, 34% or more, 36% or more, 38% or more, 40% or more, 42% or more, 44% or more, 46% or more, 48% or more, 50% or more, 52% or more, 54% or more, 56% or more, 58% or more, 60% or more, 65% or more, 70% or more or 80% or more, or 80% or less, 70% or less, 65% or less, 60% or less, 58% or less, 56% or less, 54% or less, 52% or less, 50% or less, 48% or less, 46% or less, 44% or less, 42% or less, 40% or less, 38% or less, 36% or less, 34% or less, 32% or less, 30% or less, 28% or less, 26% or less, 24% or less, 22% or less, 20% or less, 15% or less, 10% or less or 5% or less, as compared to before the stretching.

In an aspect of the present disclosure, the composition containing microfibrils may further contain one or more types of cells.

In the present disclosure, the "substrate" is not particularly limited as long as it is one prepared from an elastic material. For example, the elastic material may be polydimethylsiloane (PDMS). However, any elastic material widely known in the art may be used without limitation.

In the present disclosure, "elasticity" means the ability of an object to return to its original structure after its structure has been deformed by an external force, as obviously recognized by those skilled in the art. Specifically in the present disclosure, the "elastic substrate" may mean a substrate which, after it has been stretched by 5% or more, 10% or more, 15% or more, 20% or more, 30% or more, 35% or more, 40% or more, 45% or more, 50% or more, 55% or more, 60% or more, 70% or more or 80% or more of its width, can be restored 80% or more, 85% or more, 90% or more, 95% or more or 99% or more of its original width.

In the present disclosure, the "microfibril" refers to a fiber-like strand of sub-micrometer size, which is long, thin and bendable. The microfibril may be a synthetic or natural polymer fiber. For example, it may be a biofiber such as collagen fiber or actin fiber.

Figure 1B:
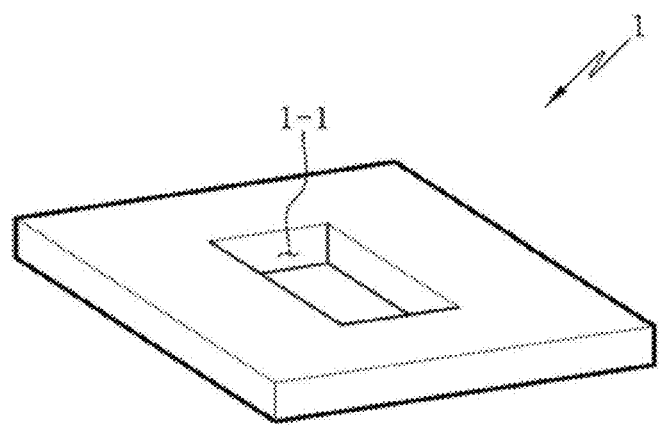
FIG. 1B shows a first elastic substrate of an apparatus for aligning microfibrils according to an aspect of the present disclosure.
Figure 1C:
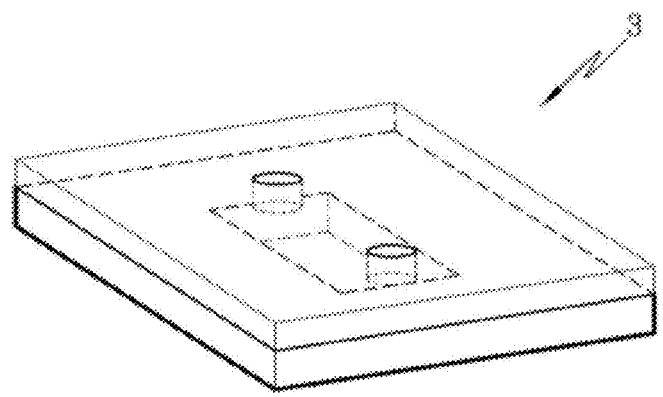
FIG. 1C shows an assembly or disassembly of a first elastic substrate and a second elastic substrate.
Figure 4A:
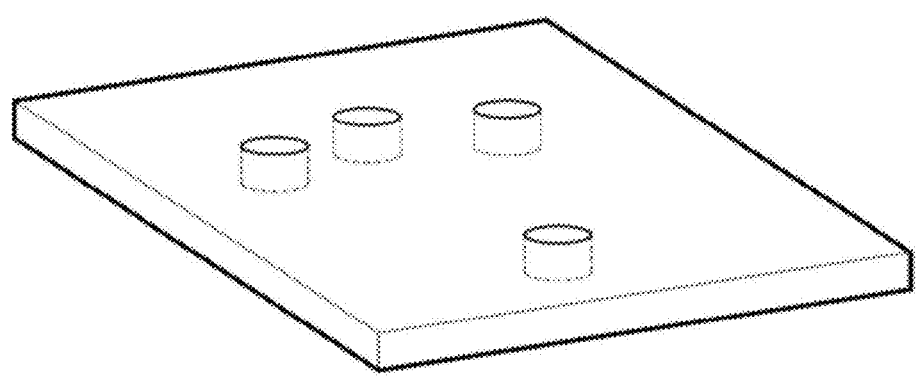
FIG. 4A shows a second elastic substrate having multiple holes.
Figure 4B:
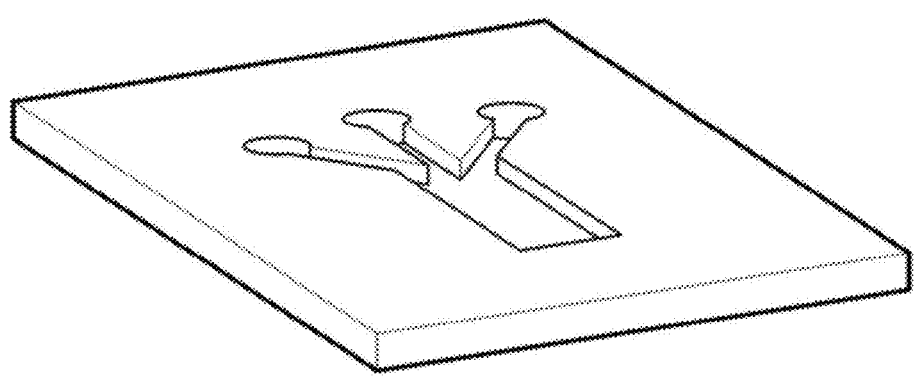
FIG. 4B shows a first elastic substrate having multiple start points.
Figure 5C:
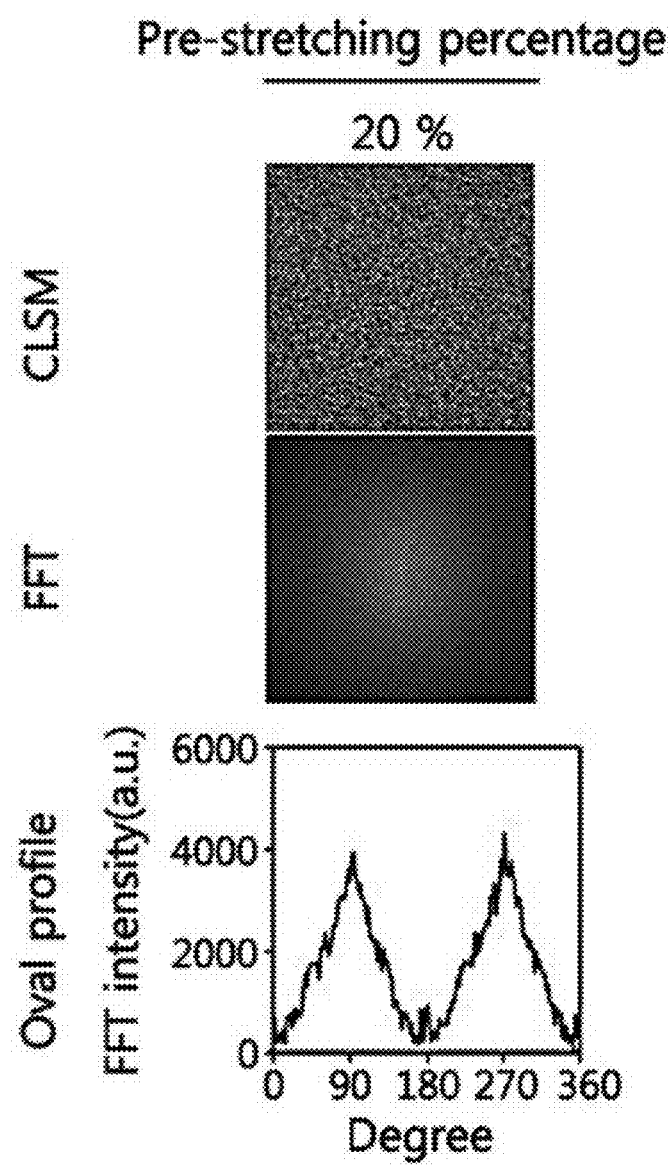
FIG. 5C shows a microscopic image and an oval profile of collagen when an elastic substrate was pre-stretched by 20% of its original width using an apparatus for aligning microfibrils of the present disclosure.
Figure 5E:
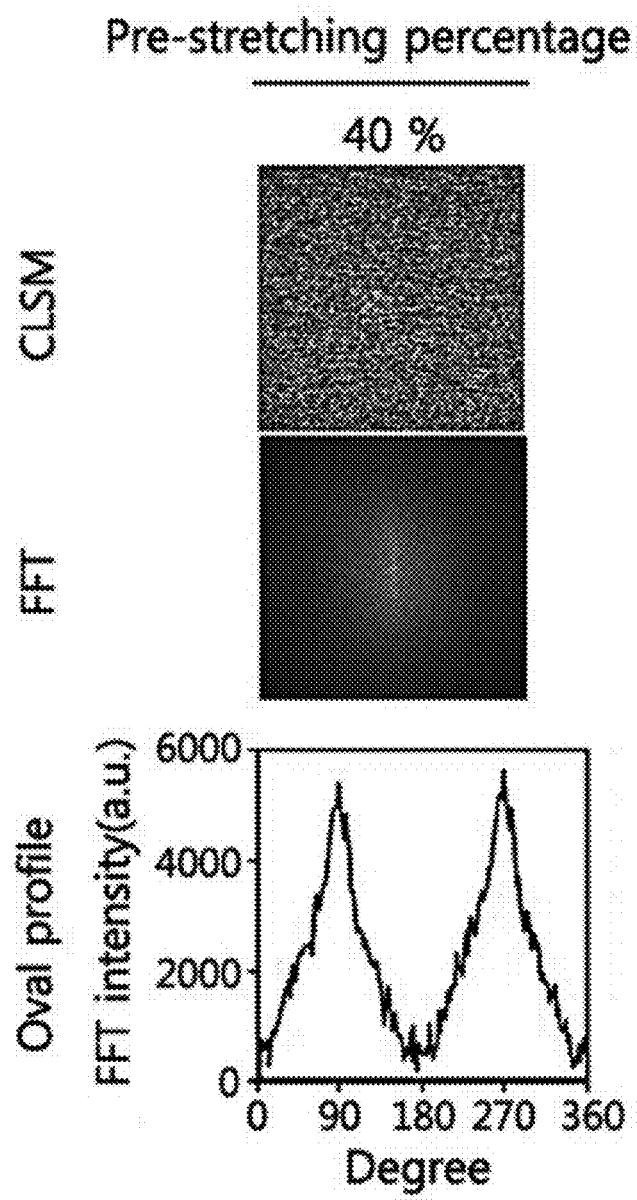
FIG. 5E shows a microscopic image and an oval profile of collagen when an elastic substrate was pre-stretched by 40% of its original width using an apparatus for aligning microfibrils of the present disclosure.
Figure 5F:
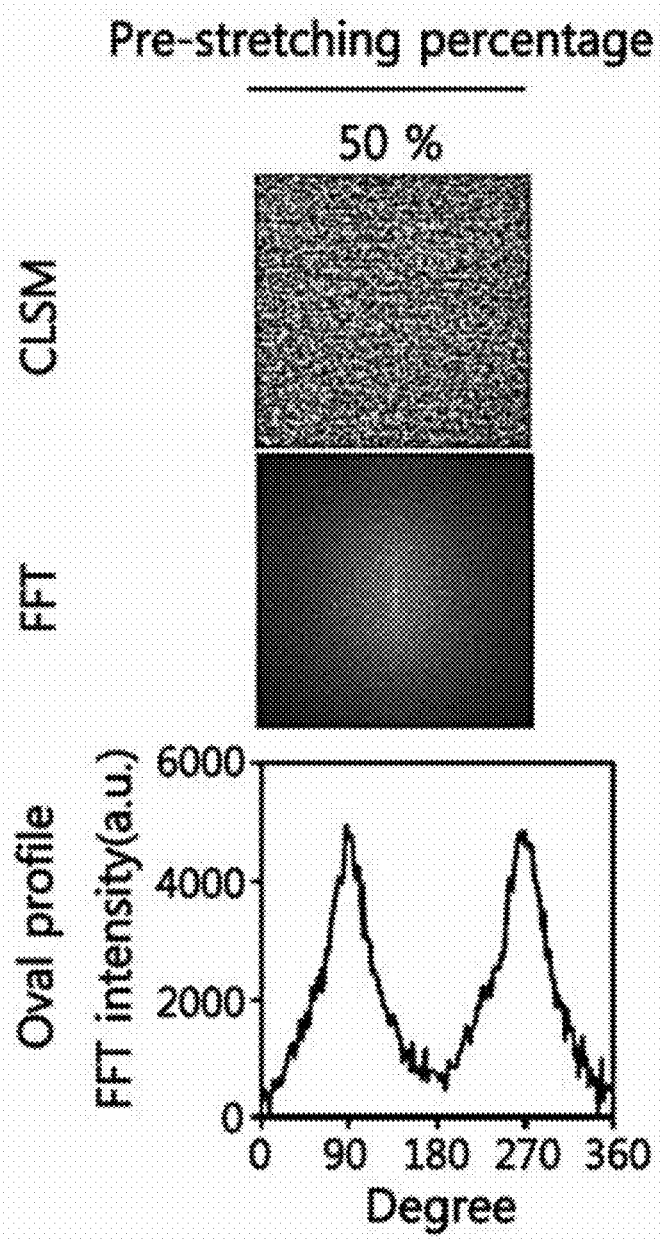
FIG. 5F shows a microscopic image and an oval profile of collagen when an elastic substrate was pre-stretched by 50% of its original width using an apparatus for aligning microfibrils of the present disclosure.
Figure 6A:
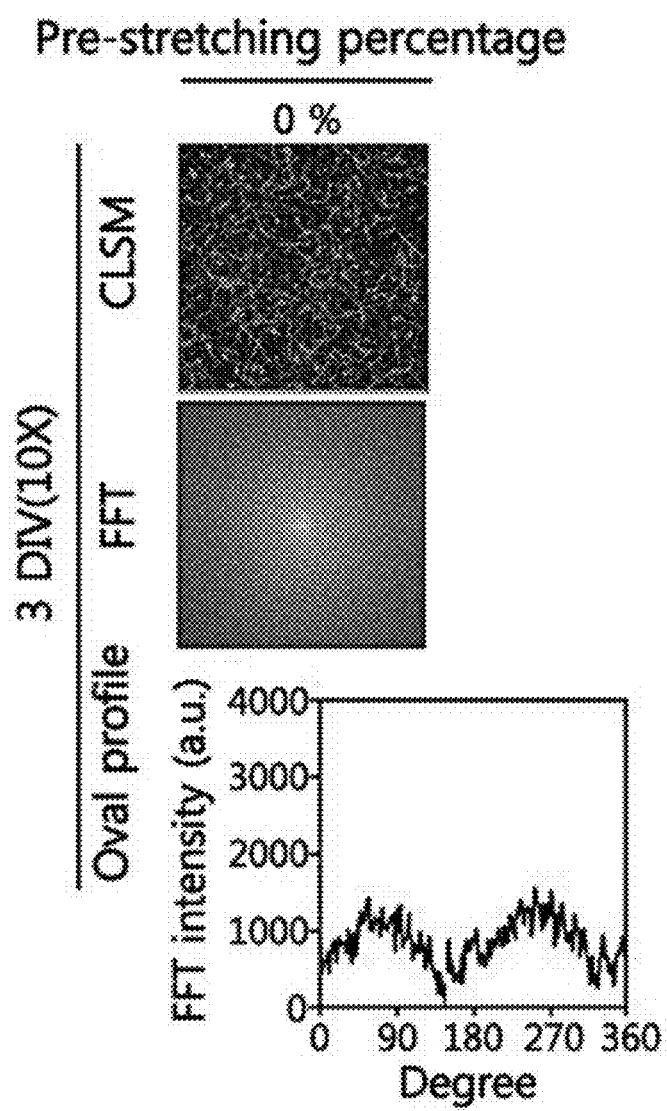
FIG. 6A shows a microscopic image and an oval profile of a mixture of collagen and cells when pre-stretching was not conducted.
Figure 6B:
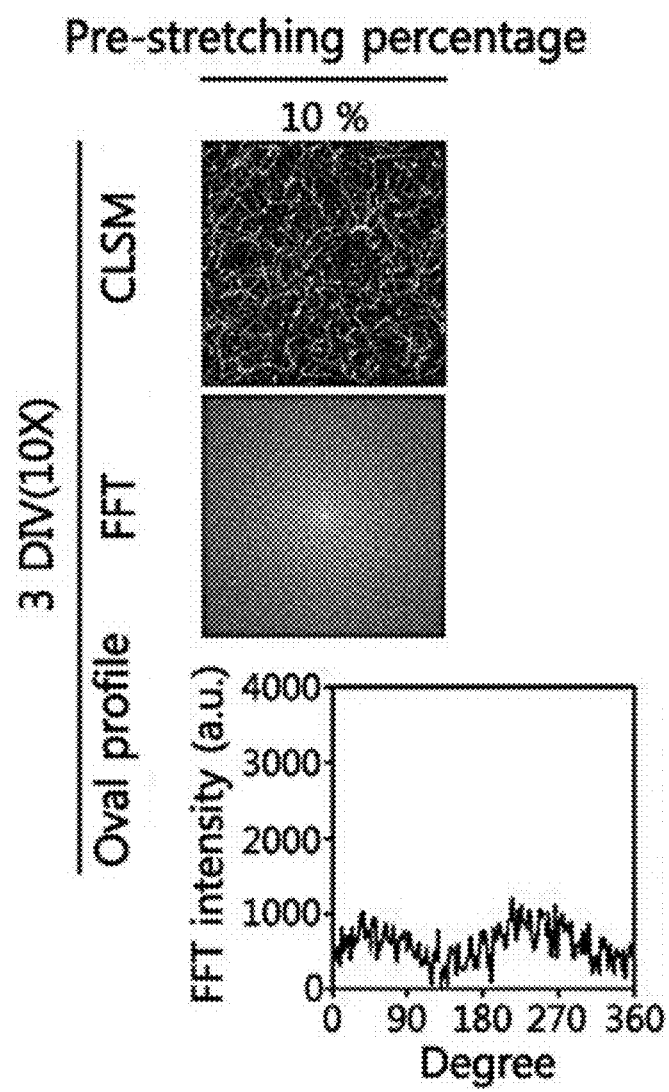
FIG. 6B shows a microscopic image and an oval profile of a mixture of collagen and cells when the cells were cultured for 3 days after an elastic substrate was pre-stretched by 10% of its original width using an apparatus for aligning microfibrils of the present disclosure.
Figure 6C:
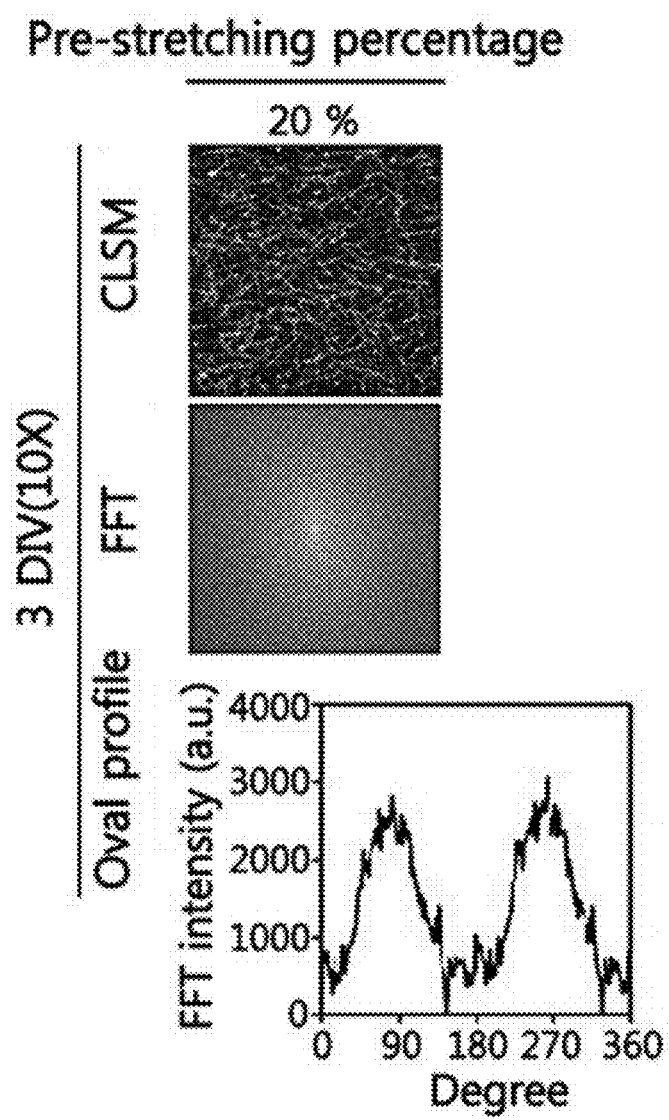
FIG. 6C shows a microscopic image and an oval profile of a mixture of collagen and cells when the cells were cultured for 3 days after an elastic substrate was pre-stretched by 20% of its original width using an apparatus for aligning microfibrils of the present disclosure.
Figure 6D:
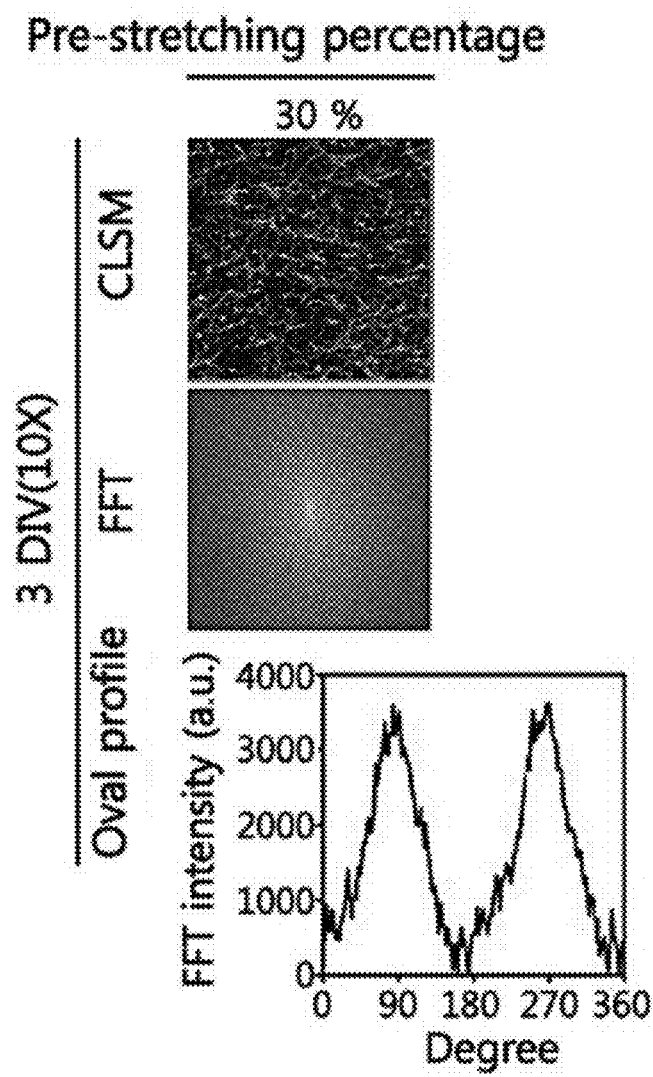
FIG. 6D shows a microscopic image and an oval profile of a mixture of collagen and cells when the cells were cultured for 3 days after an elastic substrate was pre-stretched by 30% of its original width using an apparatus for aligning microfibrils of the present disclosure.
Figure 6E:
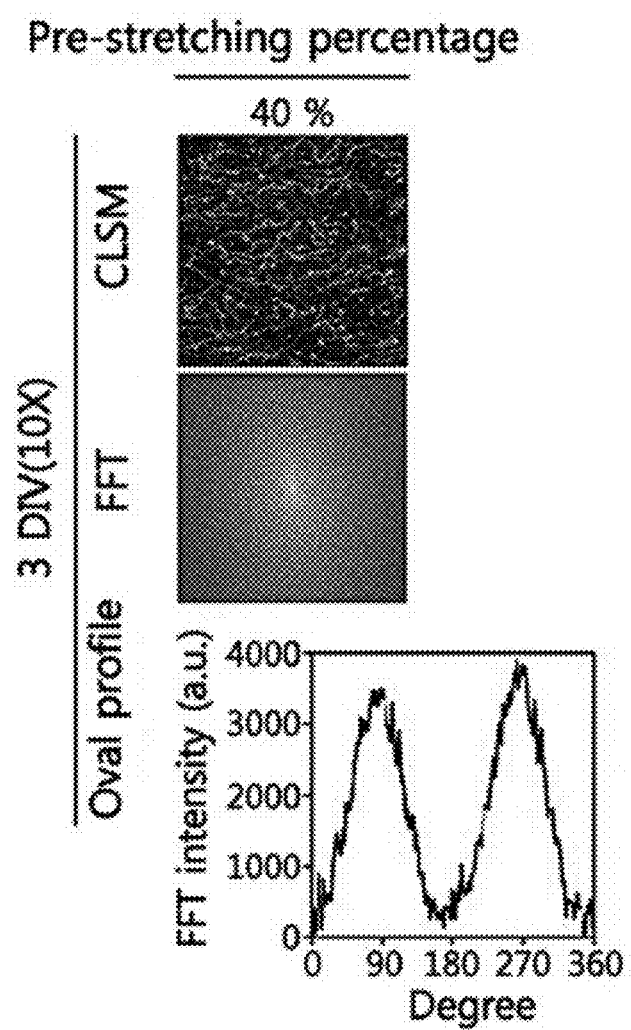
FIG. 6E shows a microscopic image and an oval profile of a mixture of collagen and cells when the cells were cultured for 3 days after an elastic substrate was pre-stretched by 40% of its original width using an apparatus for aligning microfibrils of the present disclosure.
Figure 6F:
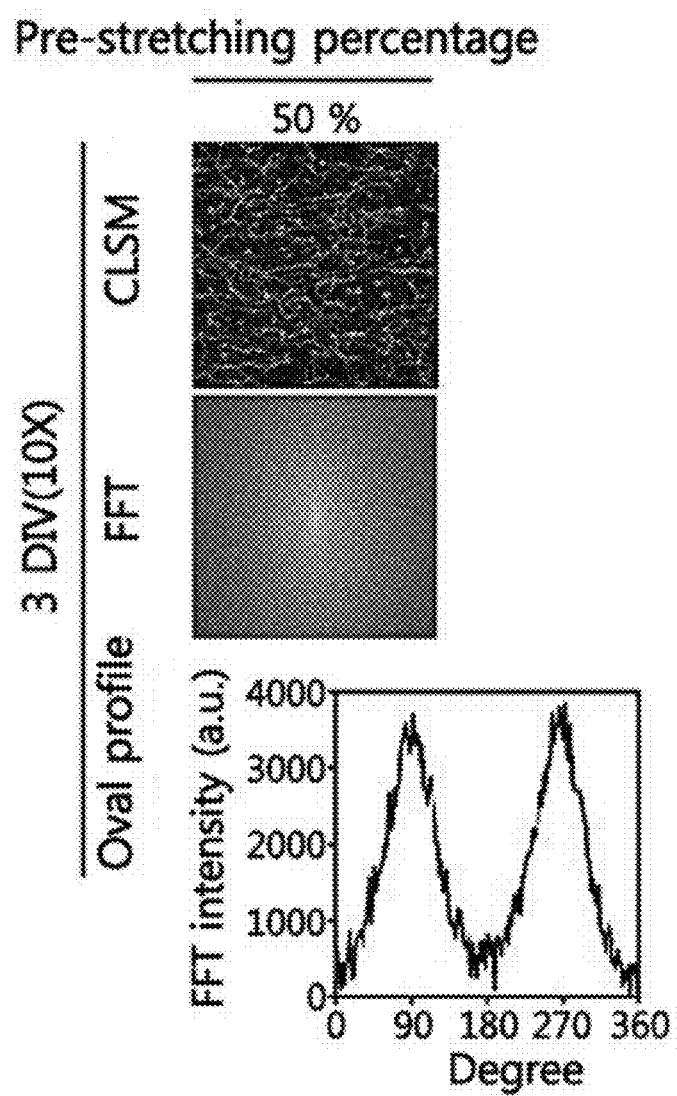
FIG. 6F shows a microscopic image and an oval profile of a mixture of collagen and cells when the cells were cultured for 3 days after an elastic substrate was pre-stretched by 50% of its original width using an apparatus for aligning microfibrils of the present disclosure.

For example, in the present disclosure, the "first elastic substrate" may have a shape as shown in FIG. 1B. Specifically, the first elastic substrate may have a well formed thereon. The size and thickness of the well are not particularly limited. When the elastic substrate has a well, microfibrils or cells loaded onto the first elastic substrate may be aligned more effectively. But, even when the elastic substrate does not have a well, microfibrils may be aligned as the substrate is stretched and then restored. Also, the shape of the well on the "first elastic substrate" of the present disclosure is not particularly limited. Specifically, when the composition containing microfibrils is a solution containing collagen or a solution containing one or more cells and collagen, the well on the first elastic substrate may have a shape wherein a single start point at which the loading of the composition containing microfibrils is started and a single end point at which the loading is accomplished are on a line. And, when the composition containing microfibrils is two or more solutions containing one or more cells and collagen, the well on the first elastic substrate may have multiple start points corresponding to the number of the loaded solutions, as in FIG. 4B. In this case, a channel may be formed for each solution such that the multiple start points of the well on the substrate converge to a single well.

In the present disclosure, the "second elastic substrate" may have a shape as shown in FIG. 1A. Specifically, the second elastic substrate may have two or more holes. When the second elastic substrate is assembled with or attached to the first elastic substrate, one or more of the holes may be present on the start point(s) of the well on the first elastic substrate and another hole may be present at the opposite location. The one or more holes are for injecting the composition containing microfibrils and are not limited in size. The another hole present at the opposite location may be present on the end point of the well of the first elastic substrate where the loading of the injected composition containing microfibrils ends and is not limited in size either. The another hole is for uniformly distributing the injected composition containing microfibrils in the well on the first elastic substrate. Specifically, it may facilitate the movement of the composition containing microfibrils by applying suction pressure.

Because the second elastic substrate is stretched and contracted together with the first elastic substrate, it may have the same elasticity and size as the first elastic substrate. In addition, the second elastic substrate may either be assembled with the first elastic substrate to form an assembly or be attached to be easily detachable.

The hole on the "second elastic substrate" of the present disclosure is not limited in shape and number. Specifically, when the composition containing microfibrils is a solution containing collagen or a solution containing one or more cells and collagen, the second elastic substrate may have two holes. And, when the composition containing microfibrils is two or more solutions containing one or more cells and collagen, the second elastic substrate may have multiple holes corresponding to the number of the loaded solutions and may have one hole to suck them on the opposite side, as in FIG. 4A.

The apparatus for aligning microfibrils according to an aspect of the present disclosure may further include a handle for stretching the first elastic substrate, which grips both ends of the first elastic substrate and has a height which is equal to or larger than the thickness of the first elastic substrate. The handle may be attached to the end portion of the upper surface of the first elastic substrate (when the height of the handle is larger than the thickness of the first elastic substrate) or to parts of both ends of the upper surface and the lower surface of the first elastic substrate (when the height of the handle is the same as the thickness of the first elastic substrate) and may serve as a handle which stretches the first elastic substrate.

In addition, when the thickness of the handle is larger than the thickness of the first elastic substrate, the apparatus for aligning microfibrils according to an aspect of the present disclosure may further include a bar or support having a height corresponding to the difference between the thickness of the handle and the thickness of the first elastic substrate. The two sides of the bar or support, i.e., its lateral and bottom sides, may be in contact with the handle and its top side may be in contact with the lower surface of the first elastic substrate. Like the handle, the bar or support may also be attached to parts of both lower ends of the first elastic substrate.

In the apparatus for aligning microfibrils according to an aspect of the present disclosure, when the first elastic substrate and the second elastic substrate are assembled to form an assembly, or an entity from which the first elastic substrate and the second elastic substrate are not easily separated, the apparatus may further include a handle which grips both ends of the second elastic substrate in order to stretch the assembly and has a height which is equal to or larger than the thickness of the assembly. The handle 5 may be attached to the upper surface of the second elastic substrate or to parts of both ends of the upper surface and the lower surface of the second elastic substrate and may serve as a handle which stretches the second elastic substrate.

In addition, the apparatus for aligning microfibrils according to an aspect of the present disclosure may further include a bar or support having a height corresponding to the difference between the thickness of the handle and the thickness of the assembly. The two sides of the bar or support corresponding to its lateral and bottom sides may be in contact with the handle and its top side may be in contact with the lower surface of the first elastic substrate. Like the handle, the bar or support may also be attached to parts of both lower ends of the first elastic substrate.

Figure 3A:
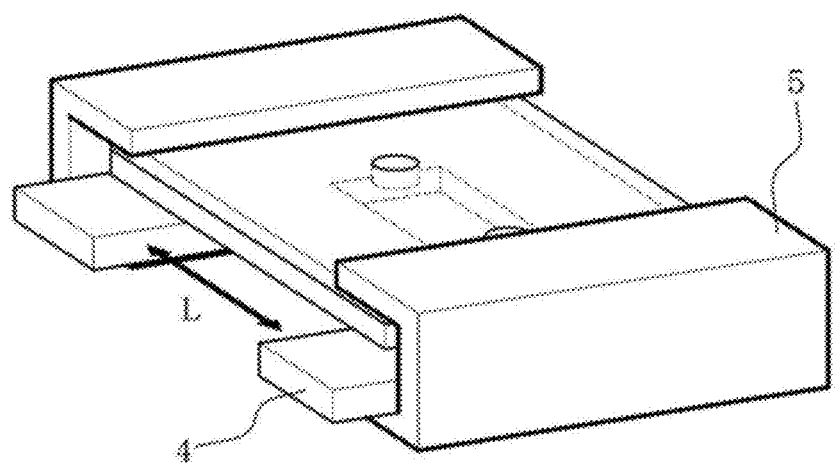
FIGS. 3A-3D show a procedure of aligning microfibrils along a single direction using an apparatus for aligning microfibrils according to an aspect of the present disclosure (A→B→C→D).

When the first elastic substrate is disassembled from the second elastic substrate, the apparatus for aligning microfibrils according to an aspect of the present disclosure may further include: a bar or support which is in contact with the both lower ends of the first elastic substrate; and a handle for stretching the first elastic substrate and the second elastic substrate, which has a height corresponding to the sum of the thickness of the first elastic substrate, the thickness of the second elastic substrate and the thickness of the bar or support. When the first elastic substrate is easily disassembled from the second elastic substrate, i.e., when they do not form an entity, it is necessary to fix the first elastic substrate and the second elastic substrate with the handle before stretching them in order to stretch them at the same time. In addition, it is also necessary to fix the bar or support to maintain the stretched state. Therefore, the height of the handle may correspond to the sum of the thickness of the first elastic substrate, the thickness of the second elastic substrate and the thickness of the bar or support. In conclusion, the apparatus may have a shape as shown in FIG. 3A.

Figure 3B:
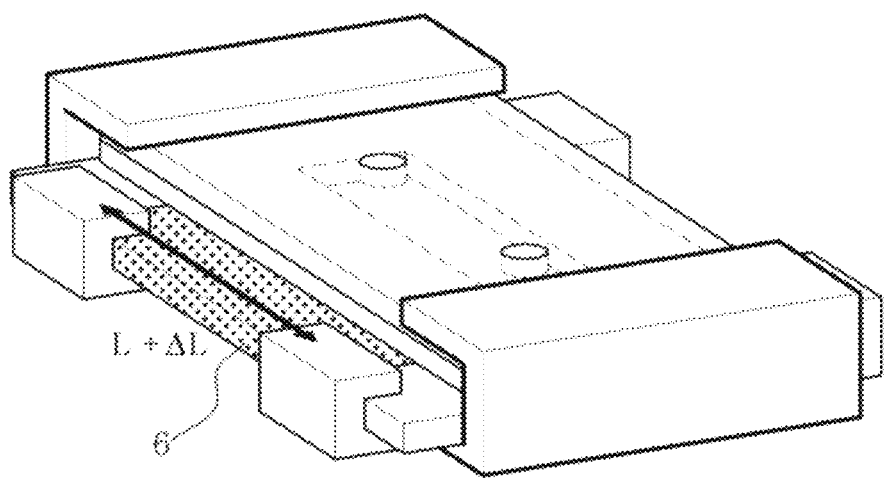

The apparatus for aligning microfibrils according to an aspect of the present disclosure may further include a fixture 6 for maintaining the stretched state of the stretched first elastic substrate or an assembly or disassembly of the stretched first elastic substrate and second elastic substrate. In order to maintain the stretched state and start loading of the composition containing microfibrils, the fixture may be disposed between the bar or support and may maintain the stretched state of the substrates. An example wherein the fixture is provided is shown in FIG. 3B.

In the apparatus for aligning microfibrils according to an aspect of the present disclosure, the composition containing microfibrils may contain microfibrils only.

In an aspect of the present disclosure, the composition containing microfibrils may be two or more compositions containing different components. One of the compositions may contain microfibrils only, and the other composition may contain microfibrils and one or more types of cells. In accordance with the apparatus or method according to an aspect of the present disclosure, the two or more compositions containing different components may be aligned at the same time.

In the apparatus for aligning microfibrils according to an aspect of the present disclosure, the cell may be a neuron or a glial cell. In accordance with the present disclosure, neurons or glial cells which are very sensitive to environmental change may be aligned and cultured without cell death.

In an aspect of the present disclosure, a method for loading the composition containing microfibrils is not particularly limited. As the substrate stretched by the method of the present disclosure is restored, the microfibrils or cells are aligned along a direction perpendicular to the stretching direction.

Figure 2:
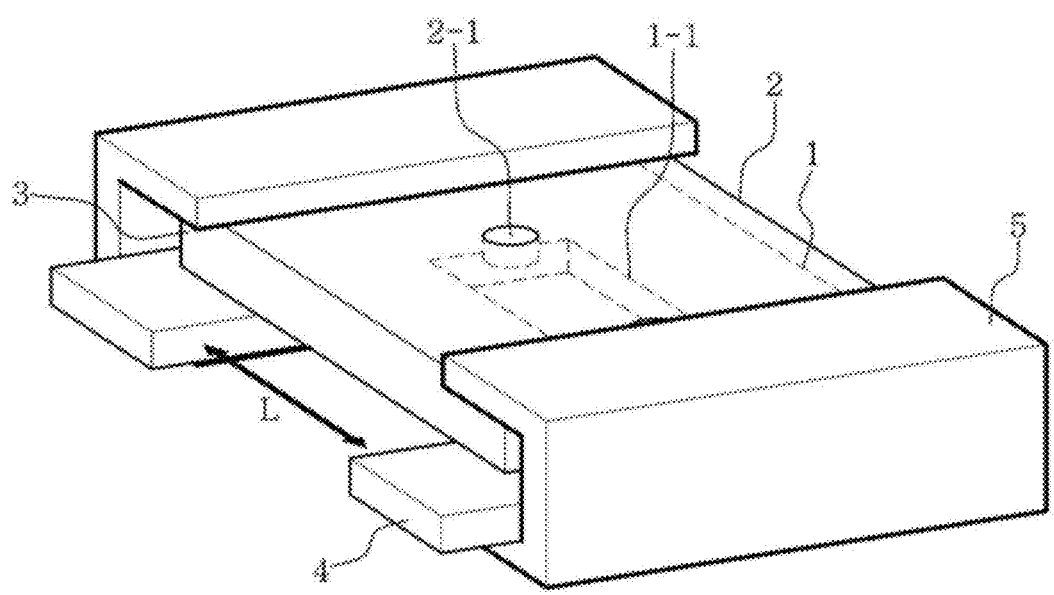
FIG. 2 shows an apparatus for aligning microfibrils according to an aspect of the present disclosure, which includes a first elastic substrate 1, a second elastic substrate 2, an assembly or disassembly 3 of the first elastic substrate and the second elastic substrate, a bar or support 4, a handle (or a grip portion) 5, a well 1-1 on the first elastic substrate and a hole 2-1 on the second elastic substrate. L represents the distance before the handle is pulled from both sides with the same pressure or after the substrate is restored to its original state.

Specifically, the apparatus according to an aspect of the present disclosure may be configured as shown in FIG. 2. Referring to FIG. 2, the apparatus may include an assembly 3 of a first elastic substrate 1 having a well 1-1 in which a composition containing microfibrils is loaded and a second elastic substrate 2 having two or more holes 2-1, and may include a support 4 which adjusts the difference in height of the assembly and a handle 5 and the handle 5 which is attached to and stretches the assembly 3 and the support 4.

FIG. 3A shows an apparatus according to an aspect of the present disclosure wherein a first elastic substrate, a second elastic substrate, a support 4 and a handle 5 are assembled with each other.

FIG. 3B shows the apparatus according to an aspect of the present disclosure wherein, after an assembly 3 of the elastic substrates has been stretched by pulling the handle, a fixture 6 is disposed between the support to maintain the stretched state. In this state, the width of the elastic substrate increases from L to L+ΔL.

Figure 3C:
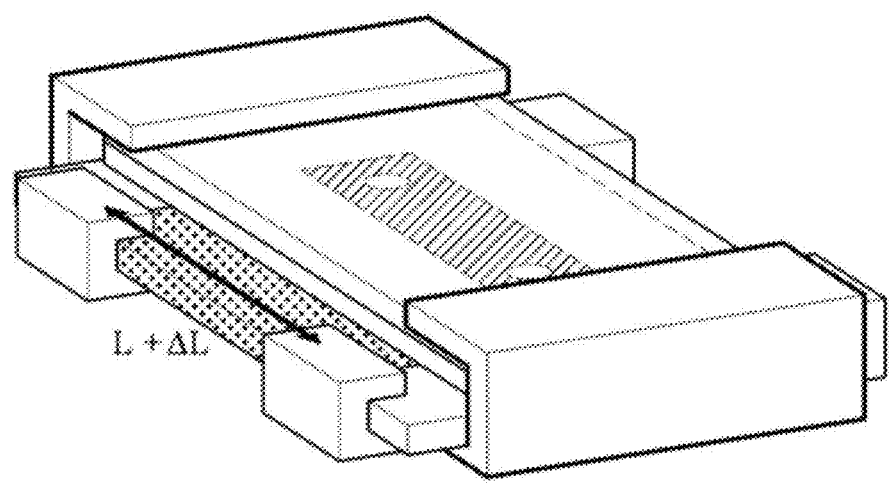

FIG. 3C shows a state wherein a composition containing microfibrils is loaded in a well of the stretched first elastic substrate.

Figure 3D:
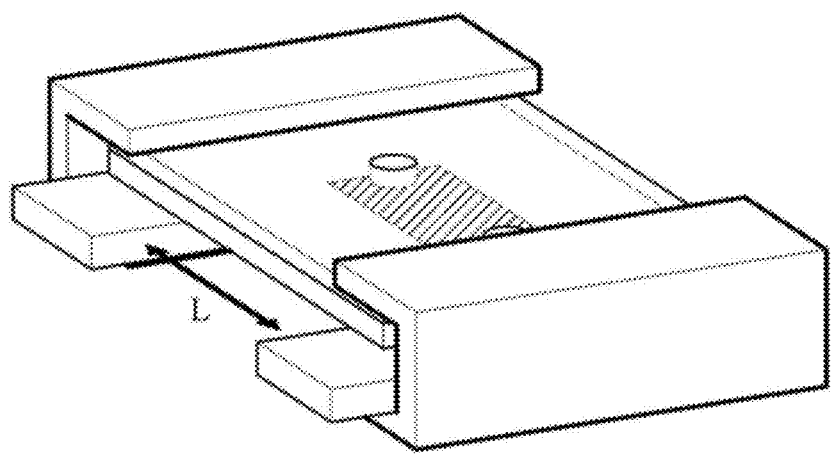

FIG. 3D shows a state wherein, after the composition containing microfibrils has been loaded and partially cured, the fixture 6 is removed to release the stretched state and the elastic substrate assembly is restored owing to its elasticity. As the elastic substrate is restored, the microfibrils or cells loaded in the well of the first elastic substrate are aligned along a direction perpendicular to the stretching direction.

Figure 9A:
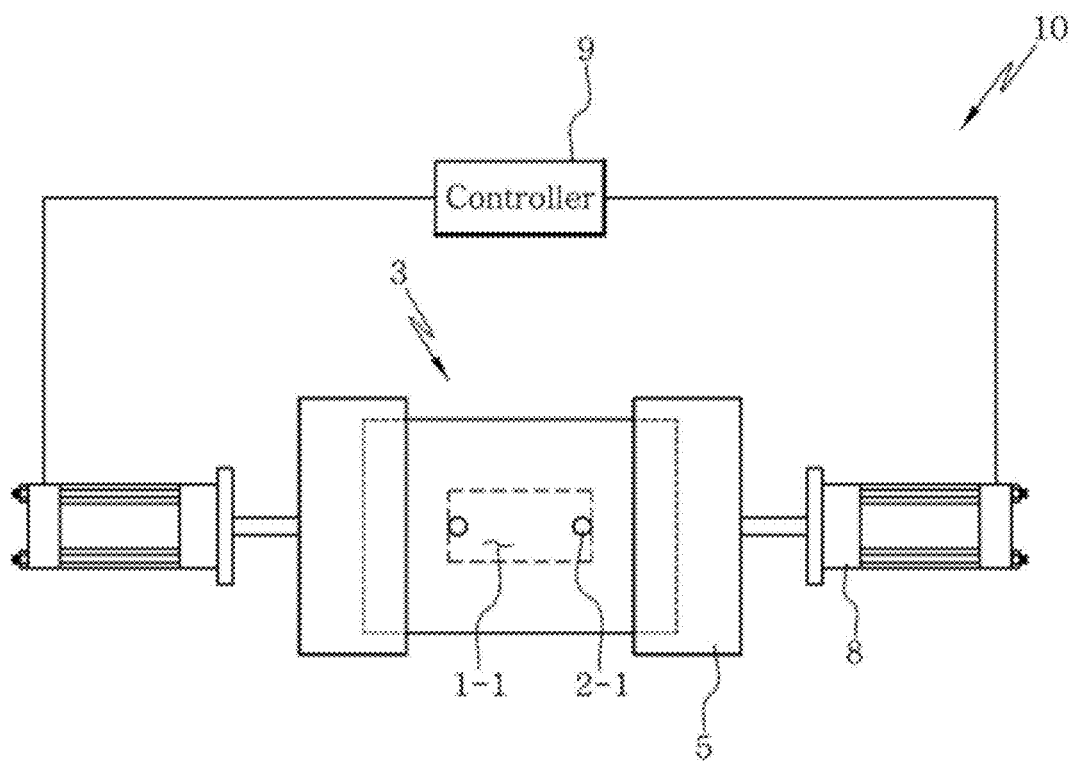
FIG. 9A shows an apparatus for aligning microfibrils according to an aspect of the present disclosure.

Specifically, the apparatus according to an aspect of the present disclosure may be configured as shown in FIG. 9A. Referring to FIG. 9A, the apparatus may include an assembly 3 of a first elastic substrate 1 having a well 1-1 in which a composition containing microfibrils is loaded and a second elastic substrate 2 having two or more holes 2-1, and a stretching module 10 which stretches the elastic substrate may include a handle 5 which is in direct contact with and stretches the elastic substrate, a stretcher 8 which operates the handle and a controller 9 which is connected to the stretcher and controls the stretching operation.

Figure 9B:
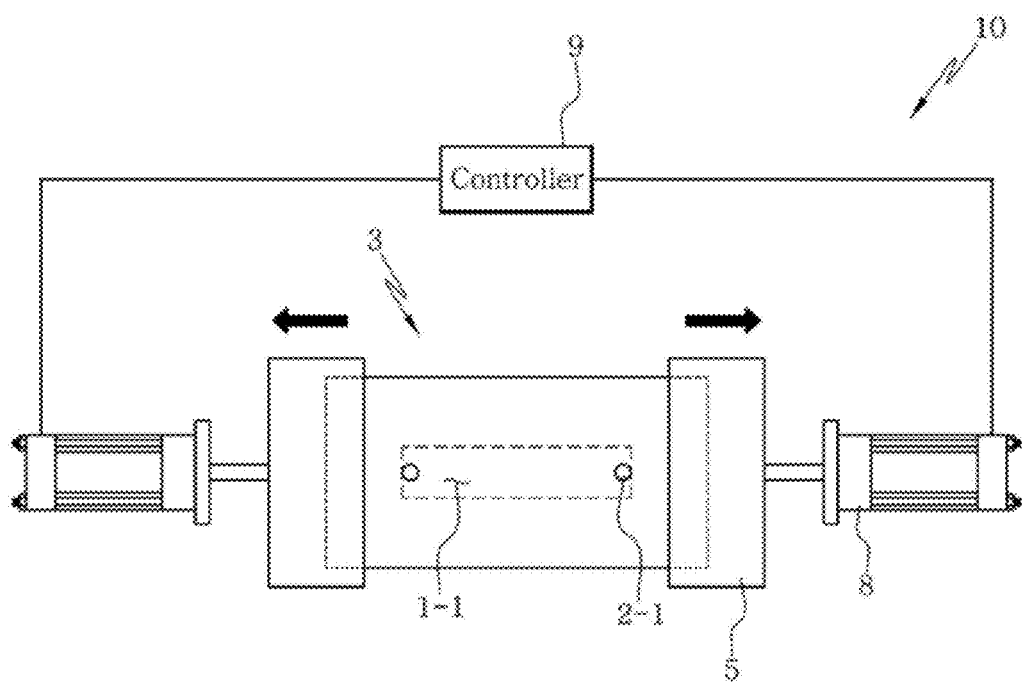
FIG. 9B shows stretching using an apparatus for aligning microfibrils according to an aspect of the present disclosure.

FIG. 9B shows stretching by the apparatus or method according to an aspect of the present disclosure. Under the control of the controller 9, the stretcher 8 operates the handle 5 and stretches the assembly 3. The stretched width and the moving time and distance of the handle are controlled by the controller. Once the stretching has been achieved as desired (e.g., 20-60% of its original width), stretching is not performed any more.

Figure 9C:
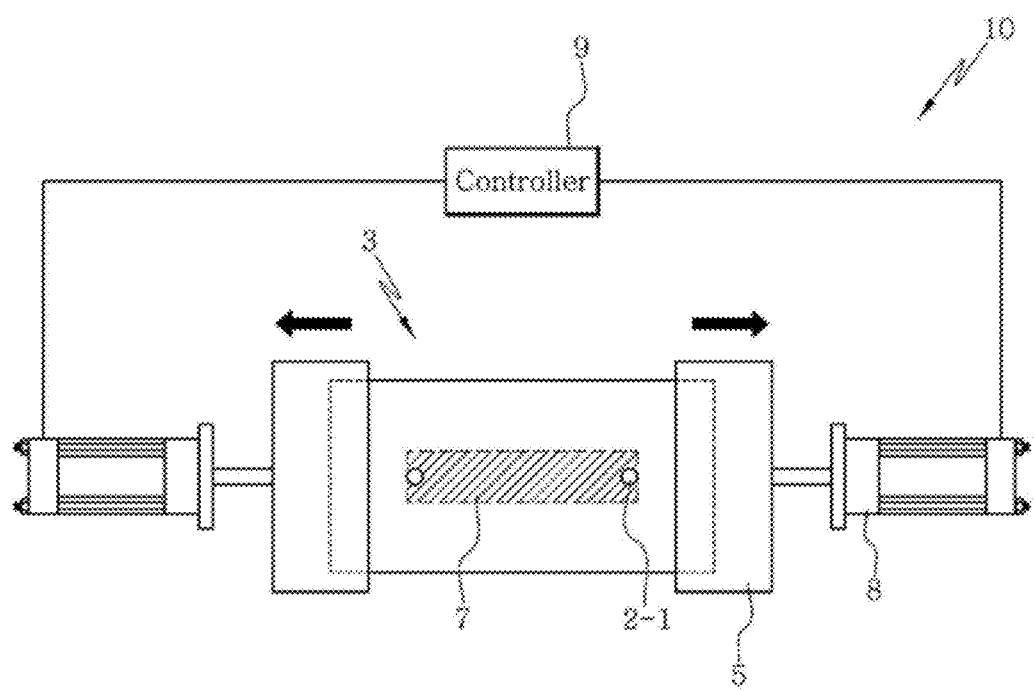
FIG. 9C shows a composition containing microfibrils loaded in a well after pre-stretching was conducted.

FIG. 9C shows loading of a composition containing microfibrils 7 in the stretched first elastic substrate 1 in the apparatus or method according to an aspect of the present disclosure. After the composition containing microfibrils 7 is loaded in the well 1-1 of the first elastic substrate, the stretched state is maintained. As the stretched state is maintained, the loaded composition containing microfibrils may be partially cured.

Figure 9D:
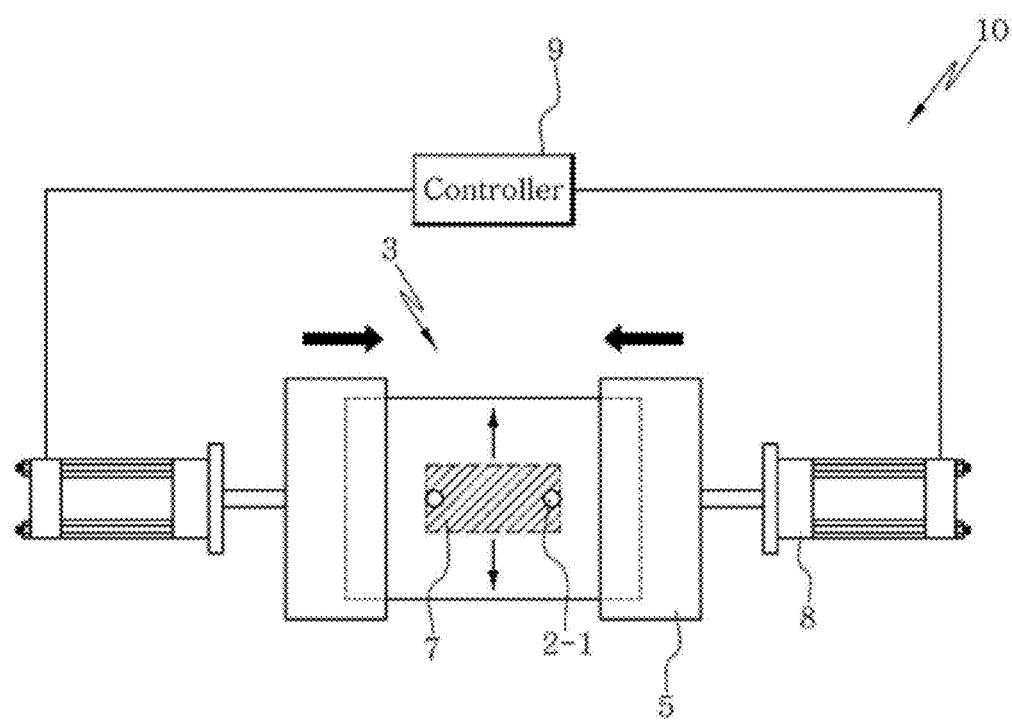
FIG. 9D shows an elastic substrate onto which the composition containing microfibrils is loaded is restored to its original state as stretching is released.

FIG. 9D shows restoring of the elastic substrate in the apparatus or method according to an aspect of the present disclosure after the stretching. The controller 9 may restore the handle 5 or release the assembly of the handle 5 and the assembly 3 in order to release the stretched state. As the assembly 3 having the composition containing microfibrils 7 loaded is restored due to its elasticity, a force perpendicular to the direction of restoring is applied to the composition and the microfibrils and cells contained in the composition containing microfibrils 7 are aligned along a direction perpendicular to the restoring direction.

Hereinafter, the present disclosure will be described in detail through examples. However, the following examples are for illustrative purposes only and it will be apparent to those of ordinary skill in the art that the scope of the present disclosure is not limited by the examples.

[Example 1] Manufacturing of Apparatus for Aligning Microfibrils

A first elastic substrate made of polydimethylsiloane (PDMS) having a well (10 mm in length, 2 mm in width, 350 μm in depth) as a substrate onto which a composition containing microfibrils is loaded, and a second elastic substrate made of polydimethylsiloane (PDMS) having holes at locations corresponding to both ends of the well as a substrate for loading the composition containing microfibrils onto the first elastic substrate were prepared. Both the first elastic substrate and the second elastic substrate were 20 mm wide, 40 mm long and 1 mm thick.

The surface of the first elastic substrate was coated with polydopamine (2 mg/mL dopamine hydrochloride in a mixed solvent (10 mM Tris-HCl buffer, pH 8.5:ethanol=9:1)) for 2 hours and then washed 5 times with distilled water, so that collagen gel can be fixed well.

The second elastic substrate was placed on and assembled with the prepared first elastic substrate. The assembly was placed on two bars, such that the both lower ends of the first elastic substrate were in contact with one side of the bars. Then, the first elastic substrate, the second elastic substrate and the bar were gripped together with a handle 5 having a thickness corresponding to the sum of the thickness of the bars, the thickness of the first elastic substrate and the thickness of the second elastic substrate.

[Example 2] Manufacturing of Apparatus for Aligning Microfibrils

An apparatus was manufactured in the same manner as in Example 1, except that the shape of the well of the first elastic substrate and the number of the holes of the second elastic substrate were changed. Specifically, in order to align collagen and two types of different cells at the same time, the first elastic substrate was prepared to have a well of a three-pronged spear (ψ) shape and the second elastic substrate was prepared to have three holes at the start points of the three-pronged spear shape and one hole at the end point thereof.

[Test Example 1] Confirmation of Alignment of Collagen Fiber

The apparatus for aligning microfibrils manufactured in Example 1 was stretched by applying the same pressure to the handle 5 in opposite directions. Then, a fixture 6 was disposed between the two bars 4 to maintain the stretched state of the first elastic substrate and the second elastic substrate.

Specifically, the first elastic substrate and the second elastic substrate whose original length was 20 mm were stretched to a length of 22, 24, 26, 28 and 30 mm. When the length was increased 2 mm (i.e., 10%) from 20 mm, the pre-stretching percentage was defined to be 10%. That is to say, the elastic substrates were pre-stretched by 10, 20, 30, 40 and 50%. A control group was not stretched (0% pre-stretching).

Collagen (fluorescence-labeled for easy monitoring of fiber alignment; collagen extracted from SD rat tail was conjugated with TRITC fluorescent dye; collagen concentration of the final collagen solution was set to 2.5 mg/mL) was injected through one hole (3 mm in diameter) of the stretched second elastic substrate. The other holes (3 mm in diameter) were blocked with needle-removed syringes so as to facilitate the injection of the collagen into the first elastic substrate. Then, the collagen was partially cured into a gel by keeping at room temperature for 5 minutes.

Subsequently, after restoring the first elastic substrate and the second elastic substrate to their original length of 20 mm by removing the fixture 6, the first elastic substrate and the second elastic substrate were separated from the apparatus. After completely gelling the collagen gel formed on the first elastic substrate by treating in an incubator at 37° C. for 30 minutes, the alignment of the collagen fiber was investigated as follows.

First, images of the TRITC-collagen gel fiber formed in the well of the first elastic substrate were obtained using a confocal microscope (FIGS. 5A-5F, CLSM). Also, in order to investigate the degree of alignment (periodicity) of the collagen fiber, fast Fourier transform (FFT) images of the confocal micrographs were obtained using the ImageJ software (FIGS. 5A-5F, FFT), and the radial sum of the FFT image intensity was analyzed with 1° intervals using the ImageJ software (FIGS. 5A-5F, oval profile).

As a result (FIGS. 5A-5F), it was confirmed that the collagen fiber was uniformly aligned along a specific direction as the pre-stretching percentage increased. In particular, the oval profiles showed sharp FFT intensity peaks at 90° and 270°, suggesting that the collagen fiber was aligned perpendicular to the stretching direction.

[Test Example 2-1] Confirmation of Alignment of Cells after Alignment of Single Collagen Solution Containing Cells Followed by Culturing The apparatus for aligning microfibrils manufactured in Example 1 was stretched by applying the same pressure to the handle 5 in opposite directions. Then, a fixture 6 was disposed between the two bars 4 to maintain the stretched state of the first elastic substrate and the second elastic substrate.

Specifically, the first elastic substrate and the second elastic substrate whose original length was 20 mm were stretched to a length of 22, 24, 26, 28 and 30 mm. When the length was increased 2 mm (i.e., 10%) from 20 mm, the pre-stretching percentage was defined to be 10%. That is to say, the elastic substrates were pre-stretched by 10, 20, 30, 40 and 50%. A control group was not stretched (0% pre-stretching).

A mixture solution of collagen (Corning® Collagen I, high concentration, rat tail, 100 mg (Product #354249)) and neurons and glial cells (derived from hippocampus of ICR mouse (18.5 embryonic days)) (final concentration of collagen in the solution=2.5 mg/mL, pH 7.5, final cell density=$2 \times 10^6$/mL) was injected through one hole of the stretched second elastic substrate. The other holes were blocked with needle-removed syringes so as to facilitate the injection of the collagen into the first elastic substrate. Then, the collagen was partially cured into a gel by keeping at room temperature for 5 minutes.

Subsequently, after restoring the first elastic substrate and the second elastic substrate to their original length of 20 mm by removing the fixture 6, the first elastic substrate and the second elastic substrate were separated from the apparatus. After completely gelling the collagen gel formed on the first elastic substrate by treating in an incubator at 37° C. for 30 minutes, the first elastic substrate was incubated for 3 days (3 DIV) with a culture medium on a culture dish.

From the cultured cells, CLSM, FFT and oval profiles were obtained in the same manner as in Test Example 1. The result is shown in FIGS. 6A-6F. Specifically, the neurons and glial cells were stained by immunostaining. For staining of the neurons, a secondary body tagged with the neuron-specific class III beta-tubulin Tuj1 and a green fluorophore was used. For staining of the glial cells, secondary body tagged with the glial fibrillary acidic protein (GFAP) and a red fluorophore was used.

As a result (FIGS. 6A-6F), it was confirmed that the neurons and glial cells were uniformly aligned along a specific direction as the pre-stretching percentage increased. In particular, the oval profiles showed sharp FFT intensity peaks at 90° and 270°, suggesting that the neurons and glial cells were aligned perpendicular to the stretching direction.

[Test Example 2-2] Confirmation of Viability of Cells after Alignment of Single Collagen Solution Containing Cells Followed by Culturing After gelling the solution loaded into the first elastic substrate in the same manner as in Test Example 2-1, the first elastic substrate was incubated for 2 hours (2 hr), 3 days (3 DIV) or 7 days (7 DIV) with a culture medium on a culture dish.

Figure 7:
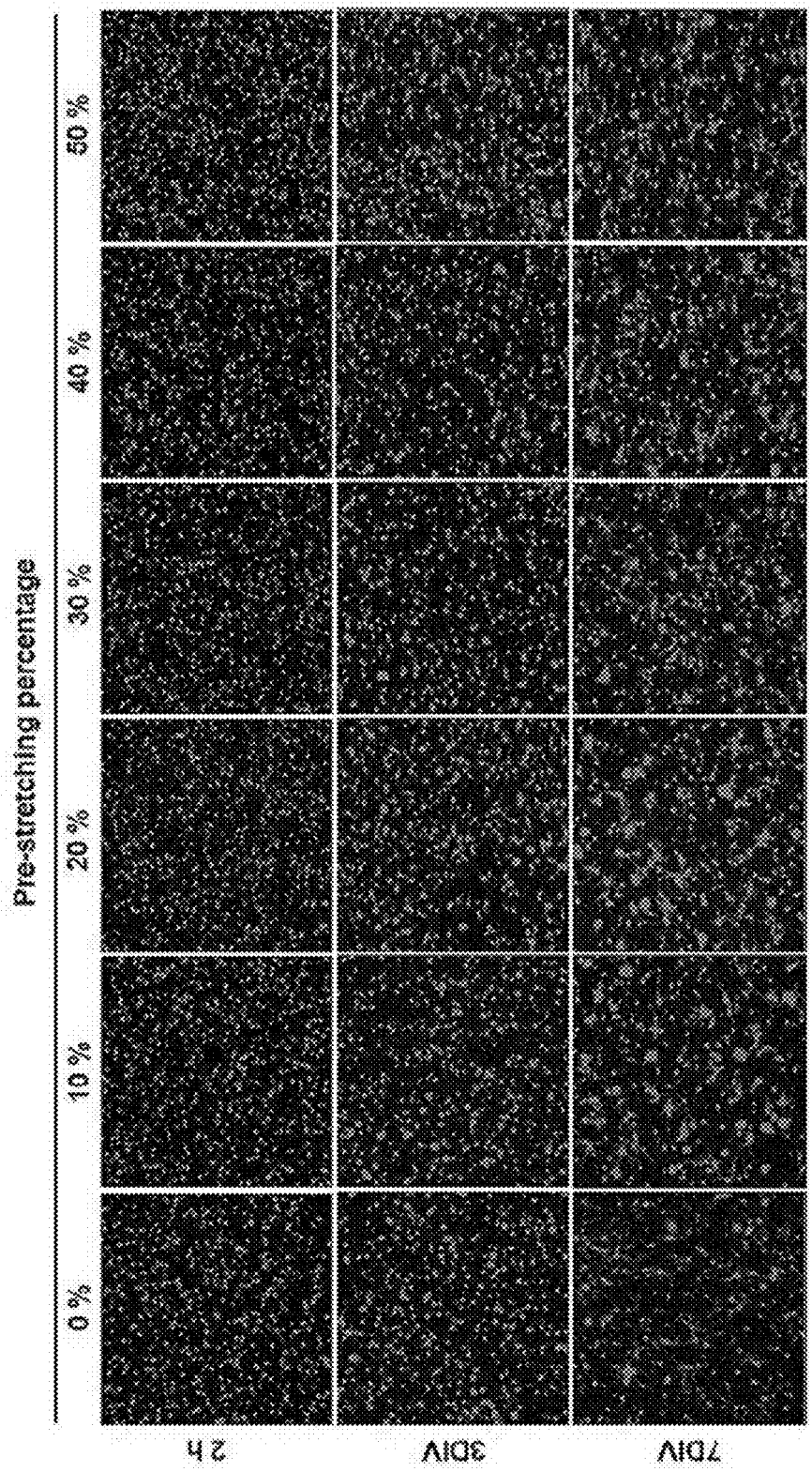
FIG. 7 shows microscopic images of a mixture of collagen and cells when pre-stretching was not conducted and when the cells were cultured for 2 hours, 3 days and 7 days after pre-stretching was conducted using an apparatus for aligning microfibrils of the present disclosure.

After the culturing, surviving cells were stained with calcein-AM and Z-stacked images were obtained using a confocal fluorescence microscope. The result is shown in FIG. 7.

As a result (FIG. 7), it was confirmed that cell viability was maintained not only immediately after the alignment of the collagen and cells but also after 7 days of culturing.

[Test Example 3] Confirmation of Alignment of Cells after Alignment of Two Collagen Solutions Containing Cells and Collagen Solution not Containing Cells Followed by Culturing The apparatus for aligning microfibrils manufactured in Example 2 was stretched by applying the same pressure to the handle 5 in opposite directions. Then, a fixture 6 was disposed between the two bars 4 to maintain the stretched state of the first elastic substrate and the second elastic substrate.

Specifically, the first elastic substrate and the second elastic substrate whose original length was 20 mm were stretched to a length of 28 mm (40% pre-stretching). CA3 hippocampal neurons isolated from the hippocampus of ICR mouse (18.5 embryonic days) were injected through the first hole (3 mm in diameter) of the three ψ-shaped holes on the stretched second elastic substrate. A collagen solution not containing cells was injected through the second hole. And, a collagen solution containing the CA1 hippocampal neurons was injected through the third hole. The other hole (3 mm in diameter) at the opposite side was blocked with a needle-removed syringe so as to facilitate the injection of the collagen into the first elastic substrate. Then, the collagen was partially cured into a gel by keeping at room temperature for 5 minutes.

Subsequently, after restoring the first elastic substrate and the second elastic substrate to their original length of 20 mm by removing the fixture 6, the first elastic substrate and the second elastic substrate were separated from the apparatus. After completely gelling the collagen gel formed on the first elastic substrate by treating in an incubator at 37° C. for 30 minutes, the first elastic substrate was incubated for 7 days with a culture medium on a culture dish.

Figure 8:
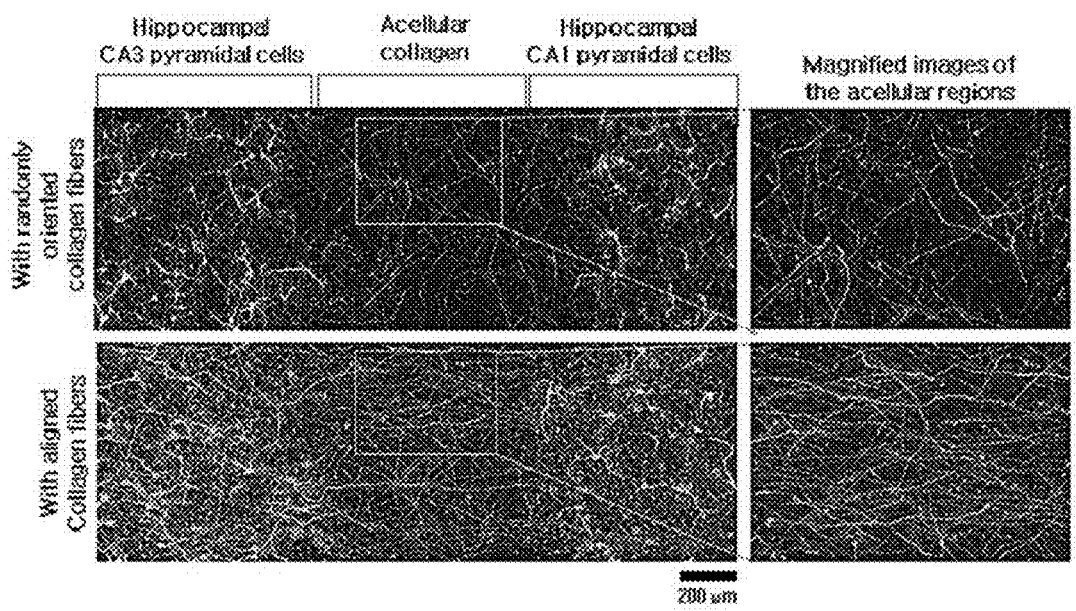
FIG. 8 shows a result of aligning collagen and two different cells along a single direction using an apparatus for aligning microfibrils of the present disclosure.

For control groups, stretching was not performed after the loading of each solution. After staining the neurites of the neurons using an anti-MAP2 antibody and TUJ1 antibody, images were obtained using a confocal fluorescence microscope (Z-stacked images were obtained as maximum projection images by scanning a thickness of 50 μm with 1-μm intervals in the Z-axis) as shown in FIG. 8.

As a result, it was confirmed that channels were formed in the first elastic substrate in the same direction for the different collagen solutions and that the channels were maintained after the culturing of the cells. From the enlarged image of the acellular collagen region in FIG. 8, it can be seen that use of the apparatus of the present disclosure resulted in alignment of the axons of the neurons and, as a result, increased neurites connection between the CA3 neurons and the CA1 neurons.

What is claimed is:

1. An apparatus for aligning microfibrils along a single direction, comprising:
   a first elastic substrate onto which a composition comprising microfibrils is loaded; and
   a stretching module which stretches the width of the elastic substrate,
   wherein the stretching module comprises: a handle which grips both ends of the first elastic substrate; a stretcher which stretches the first elastic substrate by operating the handle; and a controller which controls the movement of the stretcher, and,
   wherein the stretching module further comprises a support having a height corresponding to the difference between the height of the first elastic substrate and the height of the handle.

2. The apparatus according to claim 1, wherein the first elastic substrate comprises a well in which the composition containing microfibrils is loaded.

3. The apparatus according to claim 1, wherein the first elastic substrate comprises an elastomer.

4. The apparatus according to claim 3, wherein the elastomer is one or more selected from a group consisting of natural polyisoprene, synthetic polyisoprene, polybutadiene, chloroprene rubber, butyl rubber, styrene-butadiene rubber, nitrile rubber, ethylene propylene rubber, ethylene propylene diene rubber, epichlorohydrin rubber, polyacrylic rubber, silicone rubber, fluorosilicone rubber, fluoroelastomers, polyether block amides, chlorosulfonated polyethylene, ethylene-vinyl acetate and polydimethylsiloxane.

5. The apparatus according to claim 1, wherein the microfibril is one or more synthetic polymer fiber selected from the group consisting of nylon, polyacrylic acid, polycarbonate, polyurethane, poly(ethylene-vinyl acetate), polystyrene, polyvinyl alcohol, cellulose acetate and polyethylene oxide or one or more natural polymer fiber selected from the group consisting of elastin, gelatin, fibrinogen, fibrin, alginate, cellulose, silk fibroin, chitosan, laminin, actin and collagen.

6. The apparatus according to claim 1, wherein the composition comprising microfibrils further comprises one or more types of cells.

7. The apparatus according to claim 6, wherein the cell is a neuron, a glial cell, a muscle cell, a solid cancer cell, a mesenchymal stem cell or a fibroblast.

8. The apparatus according to claim 1, wherein the apparatus comprises a second elastic substrate which is assembled on or disassembled on the first elastic substrate.

9. The apparatus according to claim 8, wherein the second elastic substrate comprises two or more holes for loading the composition comprising microfibrils onto the first elastic substrate.

10. The apparatus according to claim 1, wherein the controller stretches the first elastic substrate by 5-80% of its width by operating the stretcher.

11. The apparatus according to claim 10, wherein the controller, after stretching the width of the first elastic substrate by operating the stretcher, maintains the stretched state for 1-10 minutes when the composition comprising microfibrils is loaded onto the first elastic substrate and then restores the first elastic substrate.

12. The apparatus according to claim 1, wherein the stretching module further comprises a fixture which is disposed between the support and maintains the stretched state of the first elastic substrate.

13. The apparatus according to claim 1, wherein the microfibrils are aligned to be perpendicular to the stretching direction of the elastic substrate.

14. The apparatus according to claim 1, wherein the first elastic substrate further comprises an adhesive coated on its surface.

15. The apparatus according to claim 14, wherein the adhesive is one or more selected from the group consisting of glutaraldehyde, polyethylenimine, poly-L-lysine, poly-D-lysine and polydopamine.

* * * * *